(12) United States Patent
Krishna

(10) Patent No.: US 11,267,708 B2
(45) Date of Patent: Mar. 8, 2022

(54) FUNCTIONALIZED FULLERENE METAL NANOCOMPOSITES

(71) Applicant: THE CLEVELAND CLINIC FOUNDATION, Cleveland, OH (US)

(72) Inventor: Vijay Krishna, Cleveland Hts., OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 178 days.

(21) Appl. No.: 16/483,096

(22) PCT Filed: Feb. 2, 2018

(86) PCT No.: PCT/US2018/016598
§ 371 (c)(1),
(2) Date: Aug. 2, 2019

(87) PCT Pub. No.: WO2018/144823
PCT Pub. Date: Aug. 9, 2018

(65) Prior Publication Data
US 2020/0231441 A1    Jul. 23, 2020

Related U.S. Application Data

(60) Provisional application No. 62/453,676, filed on Feb. 2, 2017.

(51) Int. Cl.
C01B 32/156    (2017.01)
B82Y 5/00    (2011.01)

(52) U.S. Cl.
CPC ............... *C01B 32/156* (2017.08); *B82Y 5/00* (2013.01); *C01P 2004/84* (2013.01)

(58) Field of Classification Search
CPC ..... C01B 32/156; C01B 32/152; C01B 32/15; C01B 32/18; C01B 32/154; B82Y 5/00;
(Continued)

(56) References Cited

U.S. PATENT DOCUMENTS

2008/0224100 A1*    9/2008   Smalley .............. G11C 13/025
                                                                252/510

FOREIGN PATENT DOCUMENTS

| CN | 101961785 A | 2/2011 |
| DE | 29916518 U1 | 8/2000 |
| EP | 1941887 A1 | 7/2008 |

OTHER PUBLICATIONS

Sudeep, et al., Fullerene-Functionalized Gold Nanopartiles. A Self-Assembled Protoactive Antenna-Metal Nanocore Assembly, Nano Letters 2002; 2(1): 29-35 (Year: 2002).*
(Continued)

*Primary Examiner* — Daniel C. McCracken
(74) *Attorney, Agent, or Firm* — Tarolli, Sundheim, Covell & Tummino LLP

(57) ABSTRACT

A fullerene-metal nanocomposite is described that comprises a metal nanoparticle bonded to a functionalized fullerene compound. A useful method of making a fullerene-metal nanocomposite is also described. The method consists essentially of the steps of mixing a solution of metal salt or metal ion with a functionalized fullerene compound, and purifying the fullerene-metal nanocomposite from the solution. Also described are antimicrobial surfaces, comprising a substrate surface and a coating on the substrate surface comprising a fullerene-metal nanocomposite that includes a metal nanoparticle bonded to a functionalized fullerene compound.

26 Claims, 15 Drawing Sheets

(58) Field of Classification Search
CPC ...... C01P 2004/84; A61L 2/232; A61L 2/238; A61K 31/28
See application file for complete search history.

(56) References Cited

OTHER PUBLICATIONS

"Sodium borohydride," accessed online at: https://pubchem.ncbi.nlm.nih.gov/compound/Sodium-borohydride on Mar. 22, 2021, pp. 1-34, on Mar. 22, 2021. (Year: 2021).*

"Gold(III) chloride hydrate," accessed online at: https://www.sigmaaldrich.com/catalog/search?interface=All&term=hydrogen+tetrachloroaurate(III)&N=0&mode=partialmax&focus=product&lang=en&region=US on Mar. 22, 2021 (Year: 2021).*

Ren, et al., Synthesis of fullerene@gold core-shell nanostructures, Chem. Commun. 2011; 47: 7710-7712 with Electronic Supplemtary Information (Year: 2011).*

"Gold trichloride," accessed online at https://pubchem.ncbi.nlm.nih.gov/compound/Gold-trichloride on Mar. 22, 2021 (Year: 2021).*

Lanzellotto, et al., Nanostructured enzymatic biosensor based on fullerene and gold nanoparticles: Preparation, characterization and analytical applications, Biosensors and Bioelectronics 2014; 55: 430-437 (Year: 2014).*

Al-Jumaili, Ahmed, et al. "Review on the antimicrobial properties of carbon nanostructures." Materials 10.9 (2017) 1066.

Aoshima, Hisae, et al. "Antimicrobial activity of fullerenes and their hydroxylated derivatives." Biocontrol science 14.2 (2009): 69-72.

Islam, Md Tariqul, et al. "Fullerene stabilized gold nanoparticles supported on titanium dioxide for enhanced photocatalytic degradation of methyl orange and catalytic reduction of 4-nitrophenol." Journal of environmental chemical engineering 6.4 (2018): 3827-3836.

Ren, Yupeng, et al. "Synthesis of fullerene® gold core—shell nanostructures." Chemical Communications 47.27 (2011): 7710-7712.

Sundeep, P. K., et al. "Fullerene-functionalized gold nanoparticles. A self-assembled photoactive antenna-metal nanocore assembly." Nano Letters 2.1 (2002): 29-35.

PCT International Search Report and Written Opinion for corresponding International Application Serial No. PCT/US2018/016598, dated Mar. 14, 2018, pp. 1-16.

Lanzellotto, C., et al. "Nanostructured enzymatic biosensor based on fullerene and gold nanoparticles: Preparation, characterization and analytical applications." Biosensors and Bioelectronics 55 (2014): 430-437.

European Office Action for corresponding European Application Serial No. 18704843.4, dated Aug. 19, 2020, pp. 1-8.

* cited by examiner

PHF-Metal Nanocomposite Schemes
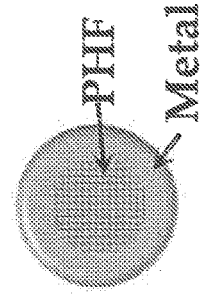
Scheme I
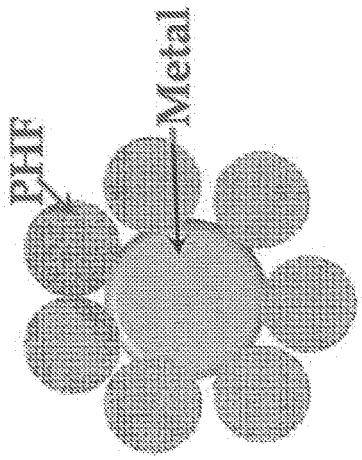
Fig. 1A
PHF coated metal nanocomposite
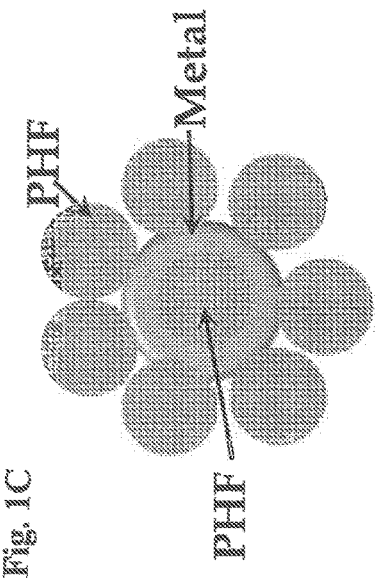
Scheme II
Fig. 1B
PHF-metal as core-shell nanocomposite
Scheme III
Fig. 1C
PHF-Metal-PHF as core-shell nanocomposite coated with PHF Fig. 13A  Oblong PHF-Gold Nanocomposites Fig. 13B  PHF-Gold Nanorods

FUNCTIONALIZED FULLERENE METAL NANOCOMPOSITES

CONTINUING APPLICATION DATA

This application claims the benefit of U.S. Provisional Application Ser. No. 62/453,676, filed Feb. 2, 2017, the disclosure of which is incorporated by reference herein.

BACKGROUND

Microbes are gaining resistance to current antimicrobials, and there is an urgent need to develop novel antimicrobial agents. The use of metal compounds such as silver in antimicrobial coatings for medical devices is known in the art. A specific advantage in using the silver ion as antibacterial agent is the inability of bacteria to acquire tolerance to the silver ion. Silver is known to possess antibacterial properties and is used topically either as a metal or as silver salts due to their ability to generate bactericidal amounts of silver ions ($Ag^+$), in which in this bioactive species, is released to the contacting environment. However, silver nitrate can cause toxic side effects, and can cause discoloration of the skin.

Metal nanoparticles have been reported to be antibacterial due to their ability to bind strongly with sulfur, which is present in enzymes and proteins. For example, gold nanoparticles with a size less than 10 nm, also known as gold nanoclusters, are redox catalysts. However, only very recently has work been carried out to study the catalytic properties of gold or other metal nanoparticles for killing microbes. Zheng et al., ACS Nano, 11, 6904-6910 (2017). This is mainly due to the very low quantum efficiency of free-radical generation by metal nanoparticles, which are suitable for reducing small organic compounds but not killing microbes. Antimicrobial polymers with metal nanoparticles have also been described. Palza H., Int. J. Mol. Sci., 16, 2099-2116 (2015).

Metal nanoparticles have been reported in several applications that utilizes their electronic properties, such as solar cell, biosensors and electronic circuits. The metal nanoparticles during synthesis have capping agents to control the size of nanoparticles. These capping agents are organic compounds that limit electron transfer between the metal nanoparticles and materials of interest (e.g., fullerene in solar cells and analytes in biosensors). Hence, majority of the research is focused on design of capping agents to enhance the electronic properties of metal nanoparticles.

SUMMARY OF THE INVENTION

The present invention provides nanocomposites comprising metal nanoparticles and functionalized fullerenes. Functionalized fullerenes include polyhydroxy fullerenes (PHF) which are water-soluble form of fullerenes. Fullerenes are spherical cages made of carbon atoms with a general formula of $C_{2n}$, where n can range from 10 to 270. The molecular formula for an unmodified PHF is $C_{2n}(OH)_x$; where x is in the range of 12 to 40. The metal nanoparticles can be made of gold, silver, copper, platinum, iron, or palladium. The metal-fullerene nanocomposites have sufficiently high catalytic activity to generate free radicals that kill microbes.

The invention also provides a method for making the metal-fullerene nanocomposites. Conventionally, metal nanoparticles are produced by reduction of their salts. For example, gold nanoparticles are produced by reduction of gold chloride with a reducing agent, such as $NaBH_4$ or $NaOH$. Other requirements for conventional methods are the need for a base to control the pH for reduction and nucleation, and the need for a capping agent to control the size of the nanoparticles. The present invention, on the other hand, provides a simpler reaction in which the functionalized fullerene serves as both a reducing agent and a capping agent. Furthermore, because reduction of the metal salts is not dependent on pH, a base is not required to neutralize the acid. As a result, the metal-fullerene nanocomposites can be produced simply by mixing the two components, while nanoparticle size and shape can be controlled by varying reactant concentrations, time, and pH.

BRIEF DESCRIPTION OF THE FIGURES

FIGS. 1A-1C provide schematic representations of various polyhydroxy fullerene-metal nanocomposites; 1A shows a PHF-coated metal nanocomposite, 1B shows a nanocomposite having a PHF core and a metal shell, and 1C shows a nanocomposite having a PHF core and metal shell that is coated with PHF.

DETAILED DESCRIPTION OF THE INVENTION

Figure 2:
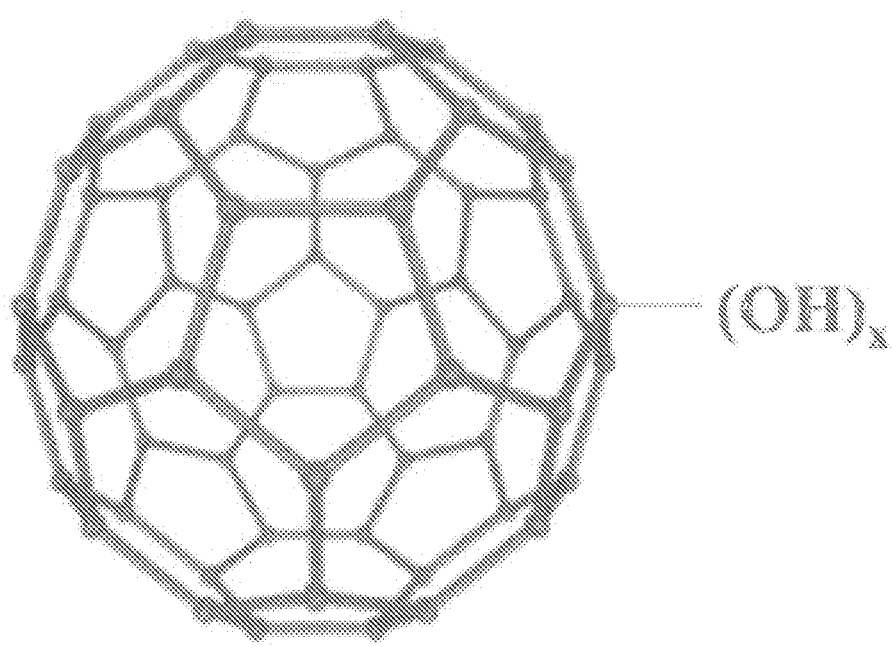
FIG. 2 provides a schematic representation of the chemical structure of a polyhydroxy fullerene (PHF) molecule (x=12 to 42).

The present invention provides a fullerene-metal nanocomposite that comprises a metal nanoparticle bonded to a functionalized fullerene compound. A useful method of making a fullerene-metal nanocomposite is also described. The method consists essentially of the steps of mixing a solution of metal salt or metal ion with a functionalized fullerene compound, and purifying the fullerene-metal nanocomposite from the solution. Also provided are antimicrobial surfaces, comprising a substrate surface and a coating on the substrate surface comprising a fullerene-metal nanocomposite that includes a metal nanoparticle bonded to a functionalized fullerene compound.

Definitions

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such.

The terms "comprising" and variations thereof do not have a limiting meaning where these terms appear in the description and claims.

The recitations of numerical ranges by endpoints include all numbers subsumed within that range (e.g., 1 to 5 includes 1, 1.5, 2, 2.75, 3, 3.80, 4, 5, etc.).

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Lower alkyl groups are those including at most 6 carbon atoms. Examples of alkyl groups include haloalkyl groups and hydroxyalkyl groups.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

When a group is present more than once in any formula or scheme described herein, each group (or substituent) is independently selected, whether explicitly stated or not. For example, for the formula —C(O)—NR$_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tent-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The term "antimicrobial" or "antimicrobial action" as used herein refers to the general term of bacteriostasis and bactericidal action. The term "bacteriostasis" or "bacteriostatic action" refers to an action of inhibiting the growth and reproduction of microbes. The term "bactericidal" or "bactericidal action" refers to an action of killing trophosomes and propagules of microbes.

The term "antimicrobial effective amount" as used herein refers to an antimicrobial amount which can achieve the desired antimicrobial action. Generally, the antimicrobial effects as needed to be achieved may be different according to different antimicrobial requirements. In some embodiments of the present application, for example, an antimicrobial effective amount of silver powders may refer to about 0.01-10% of antimicrobial nanocomposite. In some other embodiments, an antimicrobial effective amount of antimicrobial nanocomposite refers to about 0.1-5% of antimicrobial fullerene-metal nanocomposite. In other embodiments, an antimicrobial effective amount refers to about 0.5-2% of antimicrobial fullerene-metal nanocomposite.

Fullerene-Metal Nanocomposites

In one aspect, the present invention provides a fullerene-metal nanocomposite. The fullerene-metal nanocomposite includes a metal nanoparticle bonded to a fullerene compound according to the formula $C_{2n}(OH)_t(SH)_u(NH_2)_v(COOH)_w(COOM)_xO_yM_z$, wherein M is an alkali metal, alkaline earth metal, transition metal, post-transition metal, lanthanide, or actinide, n is a number ranging from 10 to 270, t is number ranging from 0 to 60, u is a number ranging from 0 to 60, v is a number ranging from 0 to 60, w is a number ranging from 0 to 60, x is a numbering ranging from 0 to 60, y is a number ranging from 0 to 30, and z is a number ranging from 0 to 30. The fullerene compound can be attached to metal nanoparticle by covalent bonds, ionic bonds, or Dewar coordination, Kubas interactions, or any combination thereof. The nature of the association between the fullerene compound and the metal nanoparticle depends on the part of the fullerene compound to which the metal nanoparticle is associating.

The nanocomposites are a combination of fullerene and metal nanoparticles. The fullerene can be combined with the metal nanoparticle in various different ways, depending on the reaction conditions used to make the fullerene-metal nanocomposite. Three different configurations for fullerene-metal nanocomposites are shown in FIGS. 1A-1C. FIG. 1A shows a PHF-coated metal nanocomposite in which the fullerene molecules are attached around a metal nanoparticle core. In this embodiment, a plurality of fullerene compounds are bonded to the outside of a metal nanoparticle core. FIG. 1B, on the other hand, shows a nanocomposite having a PHF core and a metal shell around the core. FIG. 1C shows a nanocomposite having a PHF core and metal shell that is coated with PHF. FIGS. 1B and 1C both illustrate embodiments in which a fullerene compound is within the metal nanoparticle of the fullerene-metal nanocomposite.

Functionalized Fullerenes

Functionalized fullerenes include fullerenes with functional groups attached to the outer surface of the cage via covalent bonds, ionic bonds, or Dewar coordination, or Kubas interactions, or any combination thereof. Examples of functional groups include hydroxyl, sulfhydryl, amine, and carboxyl groups. Polyhydroxy fullerenes (PHF) are water-soluble form of fullerenes including hydroxyl functional groups. Because the fullerene is "functionalized," the total of t, u, v, w, x and y must be 1 or more in order for a functional group to be present in the formula. The number of functional groups attached per cage of fullerene can vary from 1 to a majority of the number of carbons in the fullerene cage. Fullerenes are spherical cages made of carbon atoms with a general formula of $C_{2n}$, where n can range from 10 to 270. The molecular formula for a relatively unmodified PHF is $C_{2n}(OH)_t O_y M_z$; where M is an alkali metal, alkaline earth metal, or transition metal; t is in the range of 8 to 60; y is in the range of 0 to 30; and z is in the range of 0 to 30.

Functionalized fullerenes can be of a single size or can be mixtures of different fullerene sizes. The fullerene cage can be $C_{28}$, $C_{32}$, $C_{44}$, $C_{50}$, $C_{58}$, $C_{60}$, $C_{70}$, $C_{84}$, $C_{250}$, $C_{540}$, or any other fullerene. According to this nomenclature, a fullerene which contains 60 carbon atoms is denoted $C_{60}$. These correspond to functionalized fullerenes of the claimed invention wherein n is 14, 16, 22, 25, 29, 30, 35, 42, 125, and 270, respectively. Polyhydroxy fullerenes have an average of about 1.25 to 3 C atoms per OH group, which is equivalent to about 27 to about 48 OH groups on a $C_{60}$ cage. Functionalized fullerenes are often $C_{60}$ molecules due to their commercial availability, but other fullerene cages such as $C_{70}$, $C_{82}$ or their mixtures or other functionalized fullerenes can be used in various embodiments of the invention. Functionalized fullerenes have numerous C—C single bonds that can be observed by Fourier transform infrared spectroscopy (FTIR).

In some embodiments, the functionalized fullerene is a PHF according to the formula $C_{2n}(OH)_t O_y M_z$, which corresponds to the broader formula wherein u, v, w, and x are 0. The structure of unmodified polyhydroxy fullerene is shown in FIG. 2. In other embodiments, the polyhydroxy fullerene is a compound according to formula $C_{2n}(OH)_t$, which corresponds to a functionalized fullerene wherein t is 1 to 60, and u, v, w, x, y, and z are 0. In further embodiments, the polyhydroxy fullerene is a compound according to the formula $C_{2n}(OH)_t(SH)_u O_y M_z$, which corresponds to a functionalized fullerene wherein v, w and x are 0. In further embodiments, the polyhydroxy fullerene is a compound according to the formula $C_{2n}(OH)_t(NH_2)_v O_y M_z$, which corresponds to a functionalized fullerene wherein u, w and x are 0. In yet further embodiments, the polyhydroxy fullerene is a compound according to the formula $C_{2n}(OH)_t(COOH)_w O_y M_z$, which corresponds to a functionalized fullerene wherein u, v and x are 0. In additional embodiments, the polyhydroxy fullerene is a compound according to the formula $C_{2n}(OH)_t(COOM)_x O_y M_z$, which corresponds to a functionalized fullerene wherein u, v and w are 0. The specific variants within the formula are examples of the types of functionalized fullerenes encompassed by the formula, and are not meant to limit the scope of the claim to these specific examples.

The number of hydroxyl (OH), sulfhydryl (SH), amine (NH2), carboxyl (COOH), metal carboxylate (COOM), oxygen (O) and metal (M) groups can all vary between different functionalized fullerenes. For example, for hydroxyl groups, sulfhydryl groups, amine groups, carboxyl groups, and metal carboxylate groups, the number can range from 0 to 60, 1 to 60, 8 to 60, 12 to 60, 20 to 60, 0 to 50, 1 to 50, 8 to 50, 12 to 50, 20 to 50, 0 to 40, 1 to 40, 8 to 40, 12 to 40, 20 to 40, 0 to 30, 1 to 30, 8 to 30, 12 to 30, or 20 to 30, or any other ranges within 0 to 60. For the oxygen and metal groups, the number can range from 0 to 30, 1 to 30, 4 to 30, 8 to 30, 12 to 30, 0 to 20, 1 to 20, 4 to 20, 8 to 20, 12 to 20, 0 to 10, 1 to 10, and 4 to 10.

Other potential structures for functionalized fullerenes are also within the scope of the present invention. In some embodiments, the functionalized fullerenes have a formula of $C_{2n}(OH)_t O_y M1_a M2_b$; where M1 and M2 are different alkali metals, alkaline earth metals, transition metals, post-transition metal, lanthanide, or actinide; t is in the range of 0 to 60; y, a and b are in the range of 0 to 30.

In some embodiments, the functionalized fullerenes include carbon or polymer strands bound to the surface of the fullerene cage. The carbon or polymer strands can include polyethylene, polyethylene glycol, polyanhydrides, polyesters, and polyolefins. For example in some embodiments, $C_{2n}[C_m O_p H_q](OH)_t O_y M_z$; where $(OH)_t O_y M_z$ are attached to fullerene cage via the one or more carbon or polymer chains $[C_m O_p H_q]$; m is in the range of 1 to 30 and p is in the range of 0 to 15, q is in the range of 2 to 60; n is in the range of 10 to 270, M is an alkali metal, alkaline earth metal, transition metal, post-transition metal or lanthanide; t is in the range of 0 to 60; y, z are in the range of 0 to 30. In other embodiments, the functionalized fullerene is a compound according to $C_{2n}[C_m O_p H_q](COOH)_r (COOM)_s(OH)_t O_y M_z$; where carboxylic acid or metal salts are attached directly to fullerene cage or via the one or more carbon or polymer chains $[C_m O_p H_q]$; m is in the range of 1 to 30 and p is in the range of 0 to 15, q is in the range of 2 to 60; n is in the range of 10 to 270, r, s and t are in the range of 0 to 60; M is an alkali metal, alkaline earth metal, transition metal, post-transition metal or lanthanide; x is in the range of 0 to 60; y, z are in the range of 0 to 30. In further embodiments, the functionalized fullerene is a compound according to $C_{2n}[C_m O_p H_q](OH)_t(NH_2)_v O_y M_z$; where amine groups are attached directly to fullerene cage or via the one or more carbon or polymer chains $[C_m O_p H_q]$; m is in the range of 1 to 30 and p is in the range of 0 to 15, q is in the range of 2 to 60; n is in the range of 10 to 270, t is in the range of 0 to 60, v is in the range of 1 to 60, M is an alkali metal, alkaline earth metal, transition metal, post-transition metal or lanthanide; and y and z are in the range of 0 to 30.

Any of the above functionalized fullerenes can be prepared as endohedral metallofullerenes. See for example Lu et al., Chem Commun (Camb)., 50(94), pp. 14701-15 (2014), and Lu et al., Chem Soc Rev., 41(23), pp. 7723-60 (2012), the disclosures of which is incorporated herein by reference. Endohedral metallofullerenes have been made using a variety of different metals and rare earth metals, such as gadolinium, scandium, scandium-titanium, samarium, yttrium, neodymium, dysprosium, erbium, and lutetium. For example, Gd@$C_{60}$, Gd$_3$N@C60, and Sc$_3$N@$C_{80}$ are typical endohedral fullerenes.

Functionalized fullerenes may be synthesized by synthetic routes that include processes similar to those well known in the chemical arts, particularly in light of the description contained herein. See for Example U.S. Pat. No. 9,084,989, and U.S. Patent Publication No. 2007/0202413, the disclosures of which are incorporated herein by reference. A number of fullerenes are also commercially available. See for example the Fullerene Supplier Database provided online by Nanowerk™.

Metal Nanoparticles

The fullerene-metal nanocomposite includes metal nanoparticles. However, it should be understood that "metal nanoparticles," as used herein, does not require that the metal nanoparticle be a discrete particle, but rather in some embodiments can be a metal shell around a fullerene particle. The metal nanoparticle can be made of any metal. Metal groups suitable for the metal nanoparticles included in the nanocomposites of the present invention include transition metals (e.g., gold, silver and platinum), post-transition metals (e.g., aluminum, indium and lead), lanthanides (e.g., cerium, gadolinium and terbium), and actinides (e.g., uranium, thorium and plutonium). In some embodiments, the metal nanoparticle is selected from the group consisting of gold, silver, copper, platinum, iron, and palladium nanoparticles. A preferred metal nanoparticle is a gold nanoparticle.

The metal nanoparticle size can range from 0.1 nm to 150 nm. Other suitable ranges include 0.5 nm to 100 nm, 0.5 nm to 50 nm, and 1.0 nm to 50 nm. The metal nanoparticle can be in form of nanoclusters (0.1-10 nm), nanoparticles (5 nm-150 nm), nanorods, or any other crystalline shape (e.g., hexagonal, octagonal bipyramid and cubic). Metal nanoclusters consist of a small number of metal atoms, typically in the tens. A preferred size range of the metal nanoparticles, particularly for antimicrobial application, is 0.5 nm-5 nm.

Methods of Making Fullerene-Metal Nanocomposites

Another aspect of the present invention provides a method of making a fullerene-metal nanocomposite. The method consists essentially of the steps of: a) mixing a solution of metal salt or metal ion with a functionalized fullerene compound according to the formula $C_{2n}(OH)_t(SH)_u(NH_2)_v(COOH)_w(COOM)_xO_yM_z$, wherein M is an alkali metal, alkaline earth metal, transition metal, post-transition metal, lanthanide, or actinide, n is a number ranging from 10 to 270, t is number ranging from 0 to 60, u is a number ranging from 0 to 60, v is a number ranging from 0 to 60, w is a number ranging from 0 to 60, x is a numbering ranging from 0 to 60, y is a number ranging from 0 to 30, and z is a number ranging from 0 to 30 to form a fullerene-metal nanocomposite, and b) purifying the fullerene-metal nanocomposite from the solution.

The specific functionalized fullerenes and metal salts or ions can be any of the functionalized fullerenes or metals suitable for nanoparticles described herein. For example, in some embodiments, the metal salt is selected from the group consisting of gold, silver, copper, platinum, iron, and palladium salts, while in yet further embodiments the metal salt is a $HAuCl_4$. Metal salts can easily be prepared by immersing a metal in an acid or base solution, with the nature of the salt depending on the solution used. Examples of suitable salts include both inorganic and organic salts such as acetate, carbonate, chloride, citrate, cyanide, nitrate, nitrite, oxide, phosphate, and sulfate. A wide variety of salts are known to those skilled in the art. See Haynes et al., J Pharm Sci., 94(10), 2111-20 (2005). Metal ions are formed upon dissolving a metal salt in solution. Likewise, with regard to the functionalized fullerene, in some embodiments u, v, w, and x of the fullerene compound formula are 0, while in further embodiments u, v, w, x, y, and z of the fullerene compound formula are 0. In some embodiments, n of the fullerene compound formula is 30, resulting in a $C_{60}$ fullerene being used.

The key components required to make a fullerene-metal nanocomposite are the metal salt (or metal ion) and the functionalized fullerene. Furthermore, in order to make a nanocomposite, the fullerene compound(s) must have the ability to associate with the metal when mixed. Fullerene-metal nanocomposites can be made so long as functionalized fullerenes and metal salts (and/or metal ions) are mixed together in solution. Additional components can be present in the reaction mixture, so long as they don't interfere with the association of the functionalized fullerene with the metal. Interfering components can be easily avoided by those skilled in the art, or readily identified without undue experimentation. A variety of ratios of functionalized fullerene to metal salt or metal ion can be used, although different ratios can affect the amount and nature of the fullerene-metal nanocomposites that are formed. While the nanocomposites are formed upon mixing, it is generally preferable to also include a step in which the nanocomposites are purified from the reaction mixture so that the nanocomposites are substantially isolated from the reaction mixture.

Reaction of the functionalized fullerene with metal is typically carried out at room temperature. Increasing temperature speeds the reaction kinetics, while decreasing temperature can decrease the reaction kinetics and affect the particle size as well. At room temperature, the nanocomposites typically form within a few minutes. The amount of nanocomposites formed increases with time reaching the maximum in 1 hour to 12 hours depending on the temperature and the concentration of reactants.

In some embodiments, the method also includes the step of adjusting the pH of the solution. As understood by those skilled in the art, the pH (potential of hydrogen) is a numeric logarithmic scale used to specify the acidity or basicity of an aqueous solution. In different embodiments of the invention, a pH from 2 to 12 may be used for the reaction mixture. In some embodiments, it is preferable to adjust the pH to a basic value (i.e., from greater than 7 to 12) while in other embodiments, it is preferable to adjust the pH to an acidic value (i.e., from less than 7 to 2). In some embodiments, a relatively neutral pH from 6 to 8 is preferred. Acid is added to reduce the pH, while a base is added to increase the pH. A wide variety of suitable acids and bases are known to those skilled in the art. For example, a suitable acid is 1 M HCl, while a suitable base is 1 M NaOH. The pH of the solution can affect the nature and yield of the fullerene-metal nanocomposite formed by the reaction. For example, for certain functionalized fullerenes, increasing pH (~10) accelerates the reaction kinetics. In another example, decreasing the pH (~4) results in smaller size of nanocomposites.

The ratio of metal salt or metal ion to functionalized fullerene (FF) used in the method of making depends on the type and size of the desired nancomposite. The size of the nanocomposite can be varied by changing the ratio of metal ion and initial concentration of FF. The FF/metal ratio can vary from 0.01-200 mg/mL of FF to mM of metal solution. A preferred FF/metal ratio for FF-gold nanocluster is 2-200 mg/mL FF to mM metal solution. Expressing the ratios in mg/mL of FF to mM of metal ions is easier for the inventors to calculate the ratio and provides a narrower range The inventors have synthesized PHF-gold nanoclusters at ratio of 2, 7, 125 and 150 (The ratios of PHF (mg/mL) to gold chloride (mM)), which suggests that FF concentration can also have an effect on the nanocomposites formed. The FF concentration can range from 1 ng/mL to 100 mg/mL. The preferred FF concentration for FF-gold nanocluster is in the range of 1-20 mg/mL.

Figure 10:
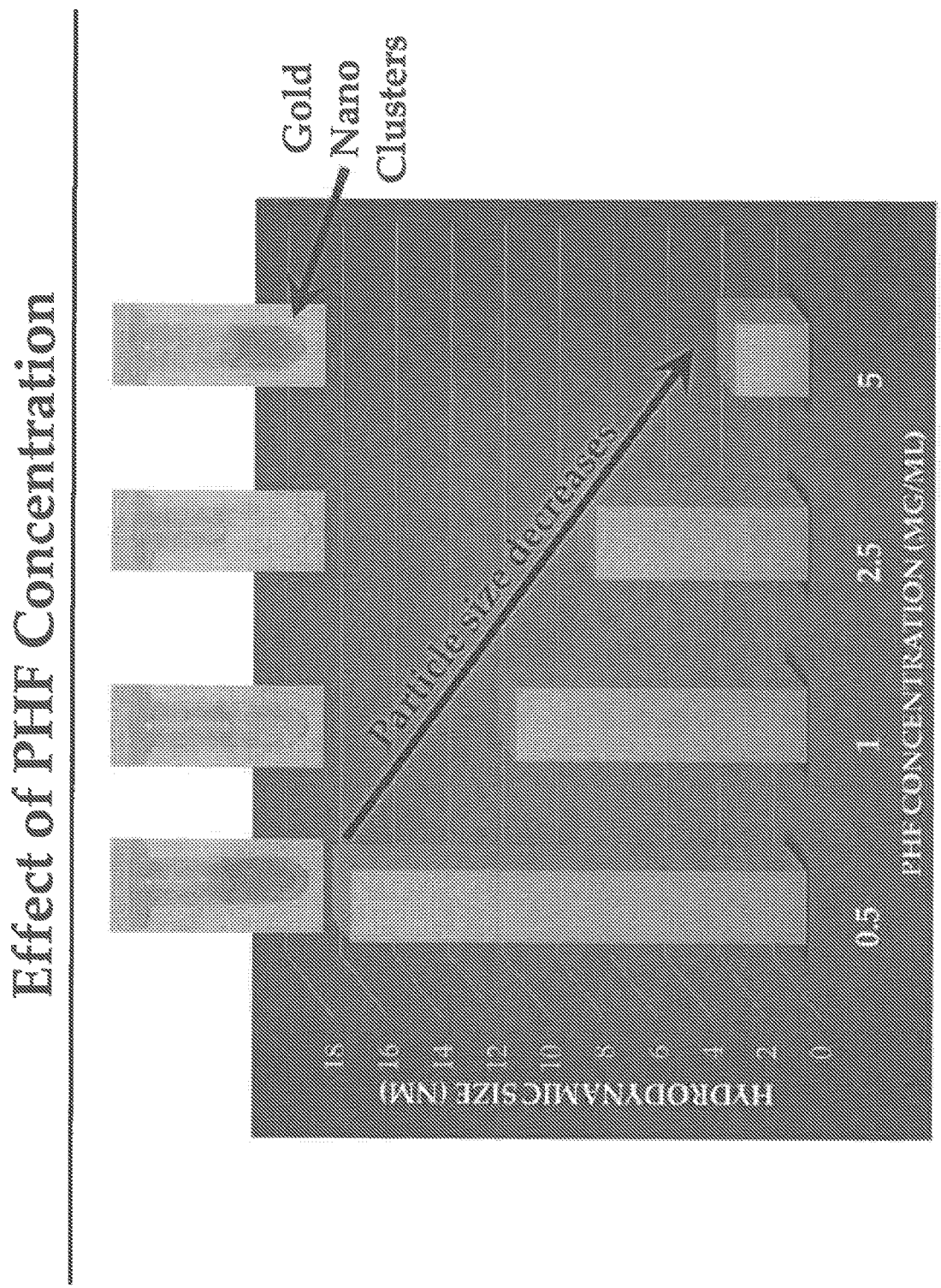
FIG. 10 provides a schematic/graphic representation showing that as PHF concentration increases, that the particle size of PHF-gold nanocomposites formed decreases.
Figure 11:
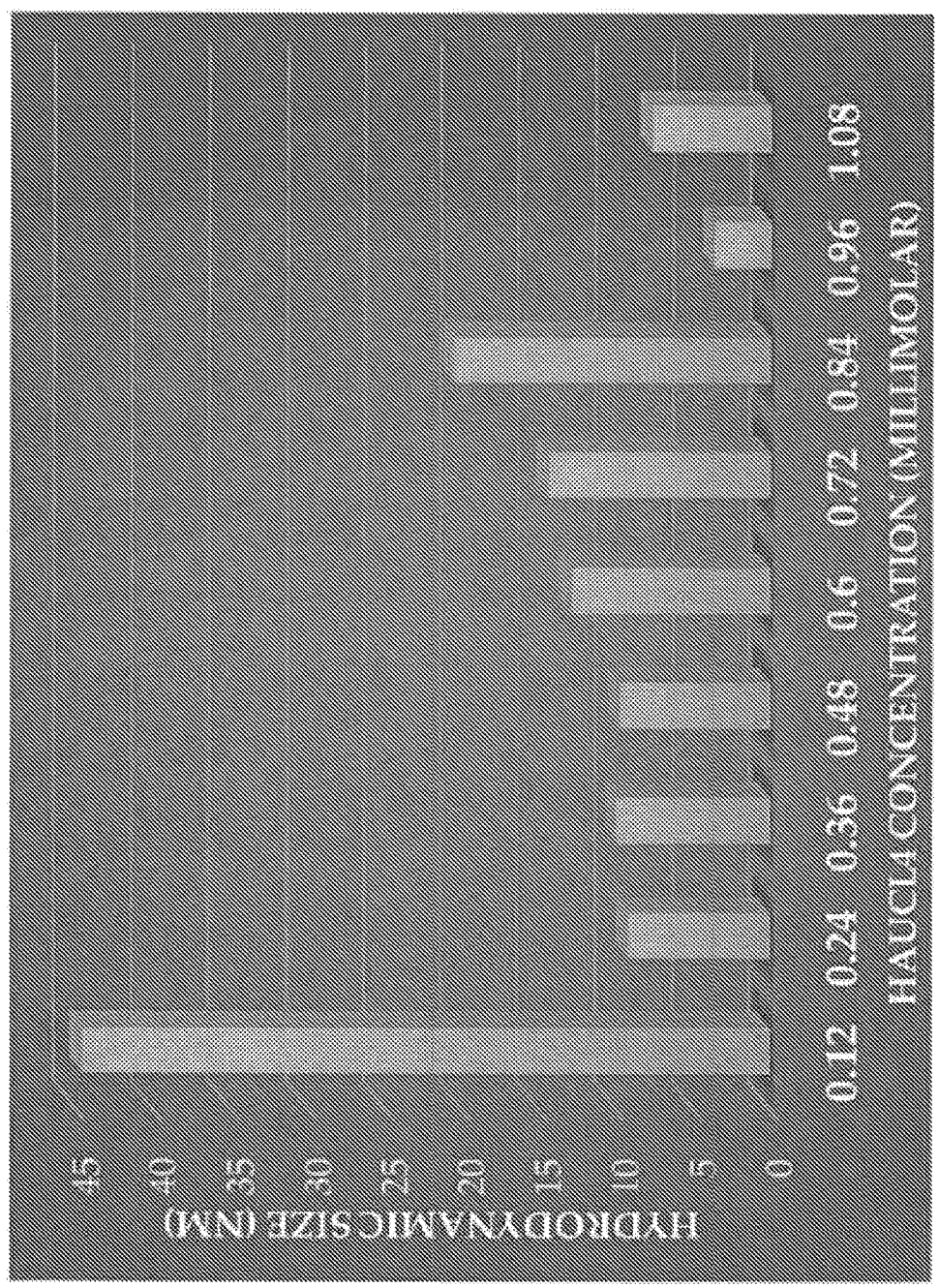
FIG. 11 provides a graph showing the effect of the concentration of a metal salt precursor (i.e., $HAuCl_4$ millimolar) on hydrodynamic size (nm).
Figure 12:
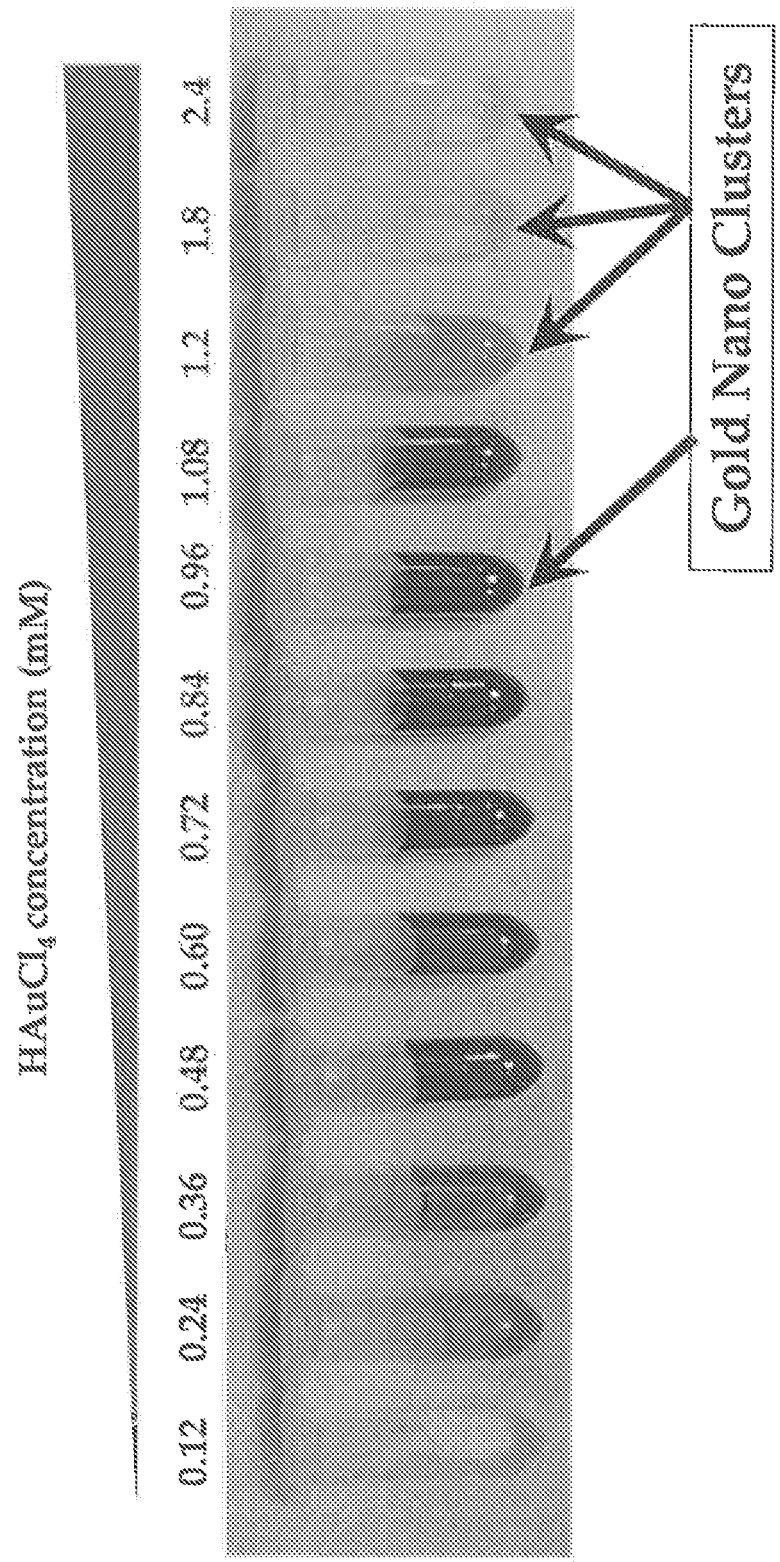
FIG. 12 provides an image showing the effect of $HAuCl_4$ concentration on PHF-gold nanoparticle nanocomposite formation.

The ability to produce a variety of different fullerene-metal nanocomposites is shown in FIGS. 10 through 12. FIG. 10 provides a schematic/graphic representation showing that as PHF concentration increases, that the particle size of PHF-gold nanocomposites formed decreases. The size of nanocomposites decrease below 5 nm at ratios greater than 20 (mg/mL of PHF to mM $HAuCl_4$). The size of gold nanoclusters decreases with increase in ratio above 20. FIG. 11 provides a graph showing the effect of concentration of a metal salt precursor (i.e., $HAuCl_4$ millimolar) on hydrodynamic size (nm). It is interesting to see that the nanocomposite size increases with increasing concentrations of $HAuCl_4$ up to 0.84 mM followed by sudden decrease at 0.96 mM, at which gold nanoclusters are formed. The nanoclusters of different size are obtained with increasing concentration above 0.96 mM. FIG. 12 provides an image showing the effect of $HAuCl_4$ concentration on PHF-gold nanocomposite formation.

Solutions and Purification

The functionalized fullerenes can be dissolved or dispersed in a solvent in order to more readily mix them as solutions. The functionalized fullerene and metal salts or ions can be dispersed or dissolved in solvent separately or together. It is known to those skilled in the art that because of the nanoscale size of functionalized fullerenes, as well as their solubility in polar and non-polar solvents, that the terms such as "dissolve," "disperse" and "suspend" can be interchangeable herein, as can be "solution," "dispersion" and "suspension," as in some cases it is not readily apparent that for the liquid phase employed if a true solution or a suspension is formed. In some embodiments of the invention, as is obvious to one skilled in the art, a solution and dispersion are distinct entities.

A variety of solvents can be used depending upon the functionalized fullerene and metal salt or metal ions used. Typically, the solvent or reaction media can be aqueous (e.g., de-ionized water or pH adjusted water), alcohol (e.g., methanol, ethanol or propanol), non-polar solvents (e.g., DMSO, dichloromethane and acetone). The preferred reaction medium for making FF-gold nanoclusters is water, while the preferred reaction medium for making FF-gold nanoparticles is a water-methanol mixture.

After the functionalized fullerene has associated with the metal salts or metal ion to form the fullerene-metal nanocomposite, the fullerene-metal nanocomposite should be purified from the solution. Examples of methods suitable for purifying nanocomposites include centrifugation, dialysis, chromatographic methods, phase transfer, and tangential flow filtration. In some embodiments, the fullerene-metal nanocomposite is purified by centrifugation or dialysis. Purified particles can be further washed to improve their purity, but obtaining 100% purity is not necessary for the nanocomposites to remain stable.

Antimicrobial Surfaces

The fullerene-metal nanocomposites described herein have antimicrobial activity, and can be included in a coating to provide an antimicrobial surface. Accordingly, a further aspect of the invention provides an antimicrobial surface. The antimicrobial surface includes a substrate surface and a coating on the substrate surface comprising a fullerene-metal nanocomposite, comprising a metal nanoparticle bonded to a fullerene compound according to the formula $C_{2n}(OH)_t(SH)_u(NH_2)_v(COOH)_w(COOM)_xO_yM_z$, wherein M is an alkali metal, alkaline earth metal, transition metal, post-transition metal, lanthanide, or actinide, n is a number ranging from 10 to 270, t is number ranging from 0 to 60, u is a number ranging from 0 to 60, v is a number ranging from 0 to 60, w is a number ranging from 0 to 60, x is a numbering ranging from 0 to 60, y is a number ranging from 0 to 30, and z is a number ranging from 0 to 30. The specific functionalized fullerenes and metal nanoparticles can be any of the functionalized fullerenes or metal nanoparticles described herein. For example, in some embodiments, the metal nanoparticle is a gold nanoparticle, while in other embodiments, u, v, w, x, y, and z of the fullerene compound formula are 0.

Substrates

The fullerene-metal nanocomposite can be applied to a surface to provide it with antimicrobial activity. In some embodiments, the fullerene-metal nanocomposite is mixed with or placed upon a carrier, such as a polymer, to provide an antimicrobial coating. The antimicrobial coating may be applied to the surface of a variety of substrate materials, including but not limited to synthetic and naturally occurring organic and inorganic polymers, plastics, metals, glass, and ceramics. While the coating formulations of the invention may applied either directly on materials with a hydrophilic surface such as metals, glass and cellulose or optionally on top of a primer undercoat, materials with hydrophobic surfaces such as silicone are subject to a surface pretreatment step prior to application of the coating.

In some embodiments, the substrate may be a device configured to be worn on a human body (e.g., jewelry, clothing, surgical gowns, masks, gloves, etc.). The substrate may be a structure configured to hold, support and/or house a subject (e.g., gurney, chair, bed, table, etc.). The coating may be applied to all or a portion of the substrate, particularly those surfaces of the substrate that may be placed in contact with a bodily fluid (e.g., a handle, supporting surface, etc.). The substrate may be a household item, such as a cutlery (e.g., spoons, baby spoons, forks, etc.), food handling items (e.g., platters, plates, straws, cups, etc.), handles (e.g., doorknobs, pushes, etc.), faucets, drains, tubs, toilets, toilet knobs, light switches, etc.

In some embodiments, the substrate surface comprises the outer surface of a medical device. The medical device may be device configured to be temporarily or permanently inserted into the body (e.g., surgical tools, implants, etc.). The substrate surface may be the outer surface of one of: a pacemaker, defibrillator, neurostimulator, or ophthalmic implant. The substrate surface may also be the outer surface of one of: an implantable shunt, an artificial joint, a hip implant, a knee implant, a catheter, a stent, an implantable coil, a pump, an intrauterine device (IUD), a heart valve, a surgical fastener, a surgical staple, a surgical pin, a surgical screw, a suture (e.g., surgical suture material, or other suture), an implantable electrical lead, or an implantable plate. The substrate surface may also be the outer surface of one of: a retractor, a bariatric balloon, an orthodontic brace, a breast implant, a surgical sponge, a gauze, a mesh pouch (e.g., mesh envelope) or a wound packing material.

In some embodiments, the substrate surface comprises a porous surface such as a membrane or porous filter. Filtration technology remains the most effective and economical means for air and water purification and disinfection. However a problem with conventional filtration technology is that microbes trapped in filters can remain viable to the extent they can grow in and colonize the filter. For example, in an air filter the warm and humid environment encourages microbial growth and presents a two-fold problem. Not only is filter performance degraded, but the colonization also poses a clear risk of contamination of the air to be filtered by the very pathogenic bacteria, viruses and fungi that the filter is designed to eliminate. Accordingly, it can be very beneficial to supply such surfaced with an antimicrobial coating to prevent colonization of the filter.

An antimicrobial coating comprising the fullerene-metal nanocomposite can be applied on porous materials and porous media. Various porous materials and porous media were used as substrates for coating with the instant antimicrobial material. Porous materials include, but are not limited to, personal protective equipment, i.e. lab coats, facial masks, shoe covers and hair caps, household products, i.e. tissues, linens, napkins, curtains and tablecloths, clothes and infant products, i.e. diapers, wipes and toys. Porous media may include membranes and filters made up of different materials such as polymers, ceramics and metals. Typical embodiments are commercial polyethylene membrane and high-efficiency particulate arrestance (HEPA) filters.

The fullerene-metal nanocomposite is applied to the surface of the substrate as a coating. Preferably, the coating readily adheres to the surface of the substrate, and retains the nanocomposite on the surface of the substrate. The fullerene-metal nanocomposites can be mixed into the coating, or placed upon the coating. In some embodiments, the coating further comprises a polymer. Suitable polymers for providing an antimicrobial coating with the fullerene-metal nanocomposite include acrylics, urethanes, methacrylates, silicones, silica precursors (tetraethyl ortho silicate), glycolates (poly ethylene glycol), styrenes, di-block and tri-block copolymers (e.g., pluronics).

The concentration of the fullerene-metal nanocomposite included in the coating can range from 1 ng/m$^2$ to 1 g/m$^2$. In some embodiments, the concentration can range from 10 ng/m$^2$ to 500 mg/m$^2$. In further embodiments, the concentration can range from 100 ng/m$^2$ to 100 mg/m$^2$. A preferred concentration range is from 1 mg/m$^2$ to 100 mg/m$^2$.

The fullerene-metal nanocomposite can be coated on surfaces by wiping, brushing, casting, dip-coating, spin-coating or spraying. The resulting antimicrobial coating exhibits the advantages of the different components displaying a multi-level, wide-spectrum and durable antimicrobial performance at broad range of temperatures. Further, the instant coatings are employed in without otherwise changing the properties and functions of the substrate. For example, a porous filter material will function as originally intended with the added benefit and result of the antimicrobial coating as described herein.

The coating thickness can range from 0.01-1000 microns. In some embodiments, the coating has a thickness from 0.1 to 1000 microns. In other embodiments, the coating has a thickness from 0.1 to 100 microns. In further embodiments, the coating has a thickness from 0.1 to 10 microns. The preferred thickness for the coating is less than 0.5 microns.

In some embodiments, a substantially smooth (i.e., uniform) coating is applied. In other embodiments, an uneven or non-uniform coating is applied. Both types of surfaces have advantages in some situations. An advantage to providing a non-uniform coating is that a greater surface area is provided that can generate a larger antimicrobial effect.

Other Applications for Fullerene-Metal Nanocomposites

Fullerene-metal nanocomposites can be used in a variety of applications other than antimicrobial use that utilizes their electronic properties, such as solar cell, biosensors and electronic circuits. During synthesis, metal nanoparticles of the prior art have capping agents to control the size of nanoparticles. These capping agents are organic compounds that limit electron transfer between the metal nanoparticles and materials of interest. For example, in design of solar cells with gold and fullerenes, the capping agents hinder the electron transfer between fullerene and gold nanoparticles and a direct contact is ideal. The present invention allows direct contact of fullerenes with metal nanoparticles providing superior properties for solar cell applications. Similarly, capping agents reduce the theoretical efficiency of biosensors and electronic circuits designed with metal nanoparticles. Functionalized fullerenes are excellent electron relays, and as a result of their direct contact with metal nanoparticles, they can overcome the drawbacks of conventional metal nanoparticles with capping agents for applications including catalysis, solar cells, biosensors, electronic circuits, thermal regulators and DNA hybridization.

The present invention is illustrated by the following examples. It is to be understood that the particular examples, materials, amounts, and procedures are to be interpreted broadly in accordance with the scope and spirit of the invention as set forth herein.

EXAMPLES

Example 1

Synthesis and Purification of PHF-AuNP

The inventors developed two different protocols for the synthesis of polyhydroxyfullerene (PHF) gold nanoparticles (AuNP). These protocols work equally well for the preparation of silver nanoparticles.

1$^{st}$ Protocol

1. Prepare stock solution of HAuCl$_4$ (or AgNO$_3$) and PHF in sterile de-ionized water.
2. Prepare working solution of HAuCl$_4$ (or AgNO$_3$):(0.1-100 mM)
3. Prepare working solution of PHF: (0.001-50 mg/mL)
4. Add 0-10 mL of 1 M NaOH or 0-10 mL of 1 M HCl to change the pH of PHF.
5. Add HAuCl$_4$ (or AgNO$_3$) solution dropwise into the glass vial containing PHF solution.
6. A color change is typically seen from few seconds to 2 hours after mixing, depending on the reaction.
7. After reaction is complete and depending on the desired particle size, add methanol and stop stirring.
8. Transfer the mixture centrifuge tubes and centrifuge at 20,000×g for 30 min.
9. One can either collect the supernatant for further reaction or discard it.
10. Re-disperse the pellets in 1:1 ratio of sterile de-ionized water and methanol.

11. Wash the pellets three times and finally resuspend in de-ionized water.
12. Store the PHF-AuNP (or AgNP) in a refrigerator at 4° C. for further characterization.

$2^{nd}$ Protocol

1. Prepare stock solution of HAuCl$_4$ (or AgNO$_3$) and PHF in sterile de-ionized water.
2. Prepare working solution of HAuCl$_4$ (AgNO$_3$): 2.425 mM
3. Prepare working solution of PHF: 2 mg/mL
4. Transfer 1 mL of PHF solution to a glass vial with stir bar. Start stirring at 300 rpm
5. Add 7.5 µL of 1 M NaOH per 1 mL of PHF to increase the pH of PHF solution to 10.
6. Add 1 mL HAuCl$_4$ (or AgNO$_3$) solution dropwise into the glass vial containing PHF solution.
7. A color change is typically seen within 15 minutes of reaction.
8. After 2 hours, add 2 mL of methanol and stop stirring.
9. Transfer the mixture to microcentrifuge tubes and centrifuge at 20,000×g for 30 min.
10. One can either collect the supernatant for further reaction or discard it.
11. Re-disperse the pellets in 1:1 ratio of sterile deionized water and methanol.
12. Wash the pellets three times and finally resuspend in deionized water.
13. Store the PHF-AuNP (or AgNP) in a refrigerator at 4° C. for further characterization.

Example 2

Analysis of Fullerene-Metal Nanocomposites

Figure 3:
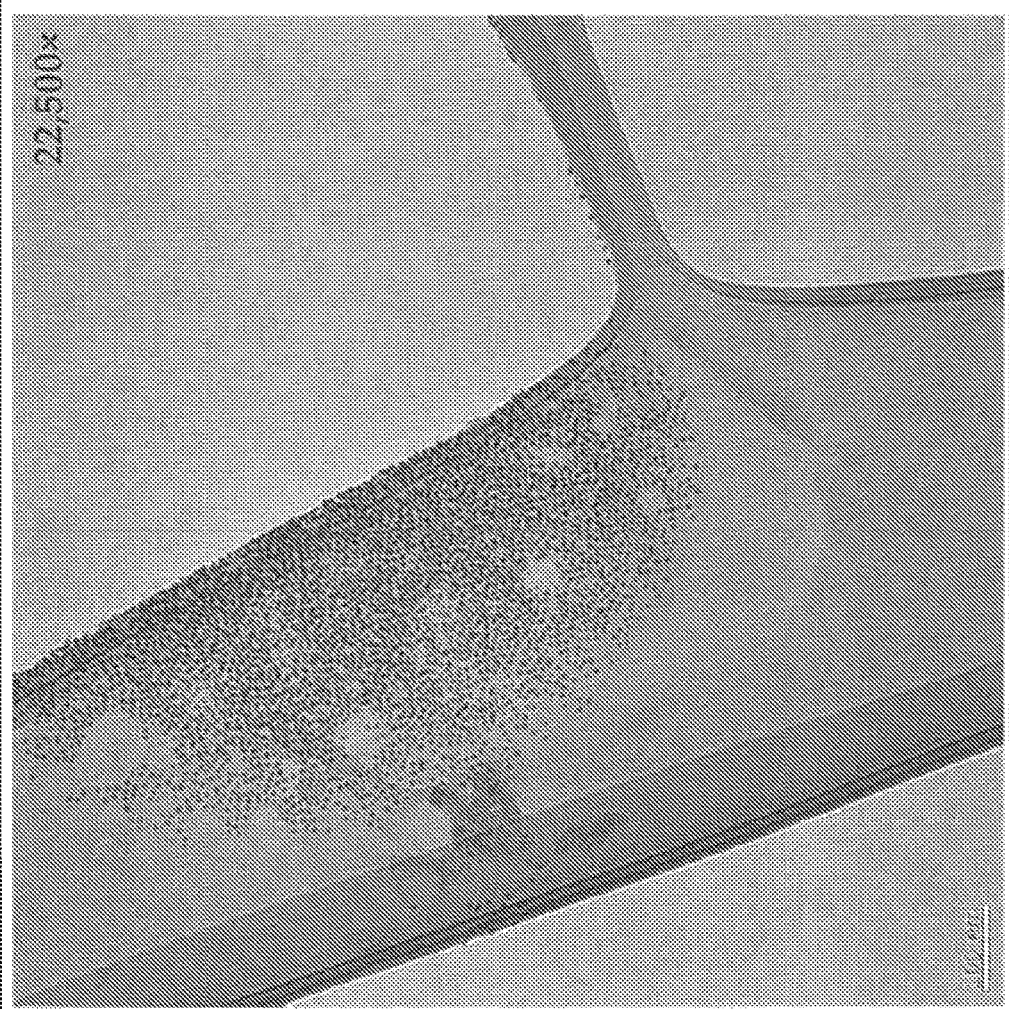
FIG. 3 provides a high-resolution transmission electron microscopy (HR-TEM) image of PHF-gold nanoparticle nanocomposites that were synthesized by simple mixing of $HAuCl_4$ and PHF, illustrating the uniform size of the nanocomposites. (Magnification 22,500×)
Figure 4:
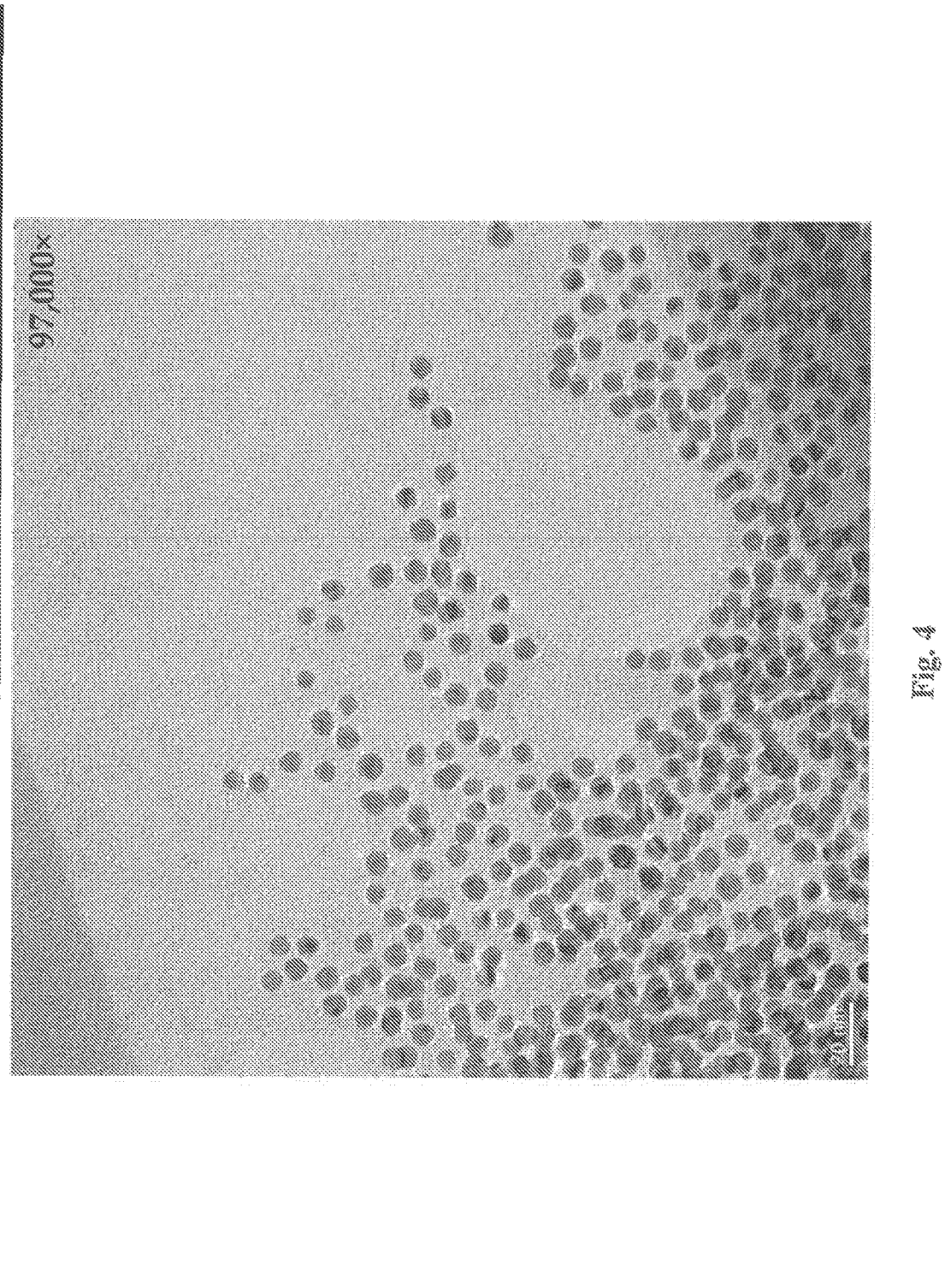
FIG. 4 provides an HR-TEM image of PHF-gold nanoparticle nanocomposites at a higher magnification. This image shows the uniform size distribution can be obtained by simple mixing of $HAuCl_4$ and PHF. (Magnification 97,000×)
Figure 5:
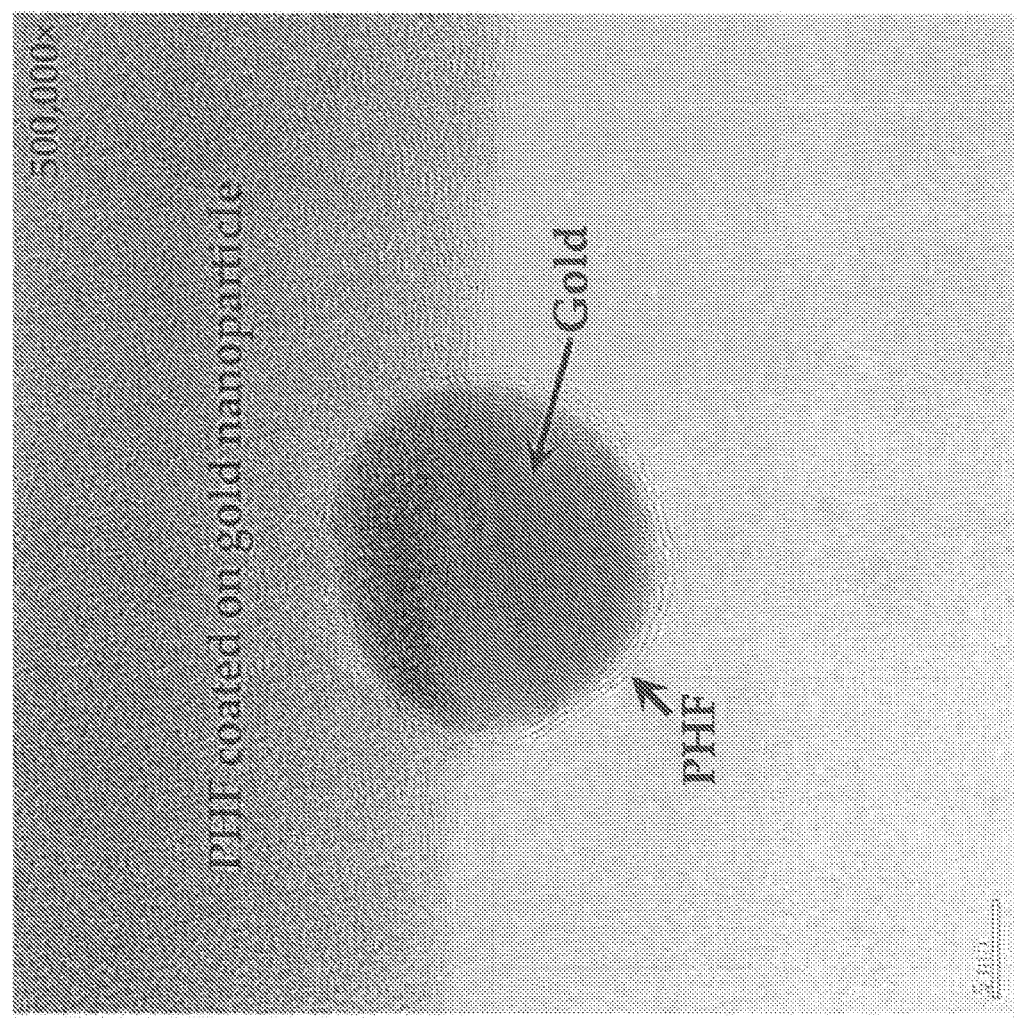
FIG. 5 provides an HR-TEM image of a single PHF-gold nanoparticle nanocomposite, showing the presence of a PHF layer surrounding a gold nanoparticle core. (Magnification 500,000×)

Fullerene-metal nanocomposites were analyzed using electron microscopy and spectroscopy in order to better characterize their structures. The nanocomposites were prepared by simple mixing of gold salts and polyhydroxy fullerenes (PHF). FIG. 3 provides a high-resolution transmission electron microscopy (HR-TEM) image of PHF-gold nanoparticle nanocomposites at a magnification of 22,500× that were synthesized by simple mixing of HAuCl$_4$ and PHF, illustrating the uniform size of the nanocomposites. FIG. 4 provides an HR-TEM image of PHF-gold nanoparticle nanocomposites at a magnification of 97,000×. This image shows the uniform size distribution can be obtained by simple mixing of HAuCl$_4$ and PHF. FIG. 5 provides an HR-TEM image of a single PHF-gold nanoparticle nanocomposite at a magnification of 500,000×, showing the presence of a PHF layer surrounding a gold nanoparticle core.

Figure 6:
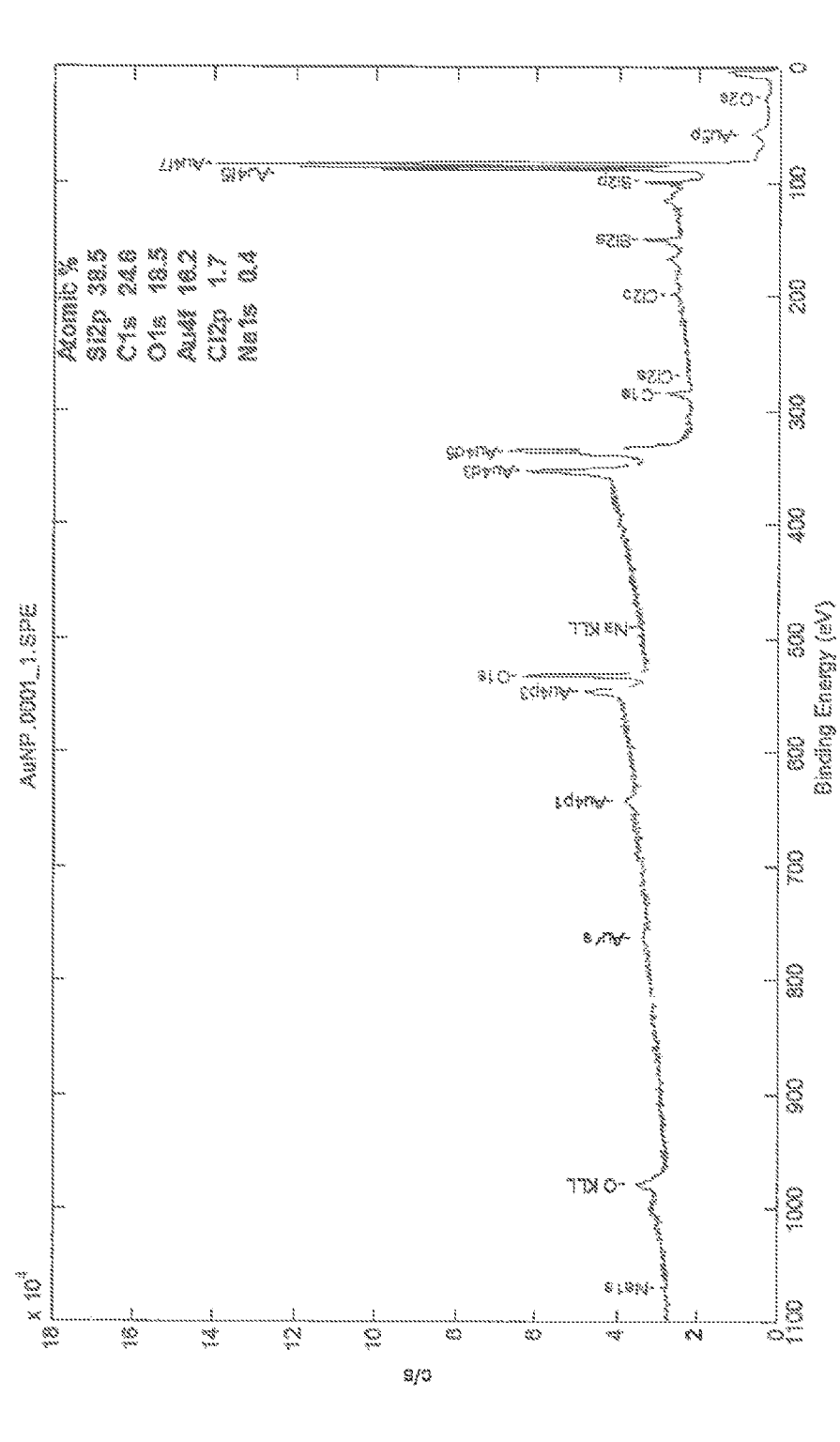
FIG. 6 provides an X-ray photoelectron spectroscopy (XPS) graph showing the type of elements found in PHF-gold nanoparticle nanocomposite. Silicon (Si) is from the substrate on which PHF-gold nanoparticles were deposited for XPS analysis.
Figure 7:
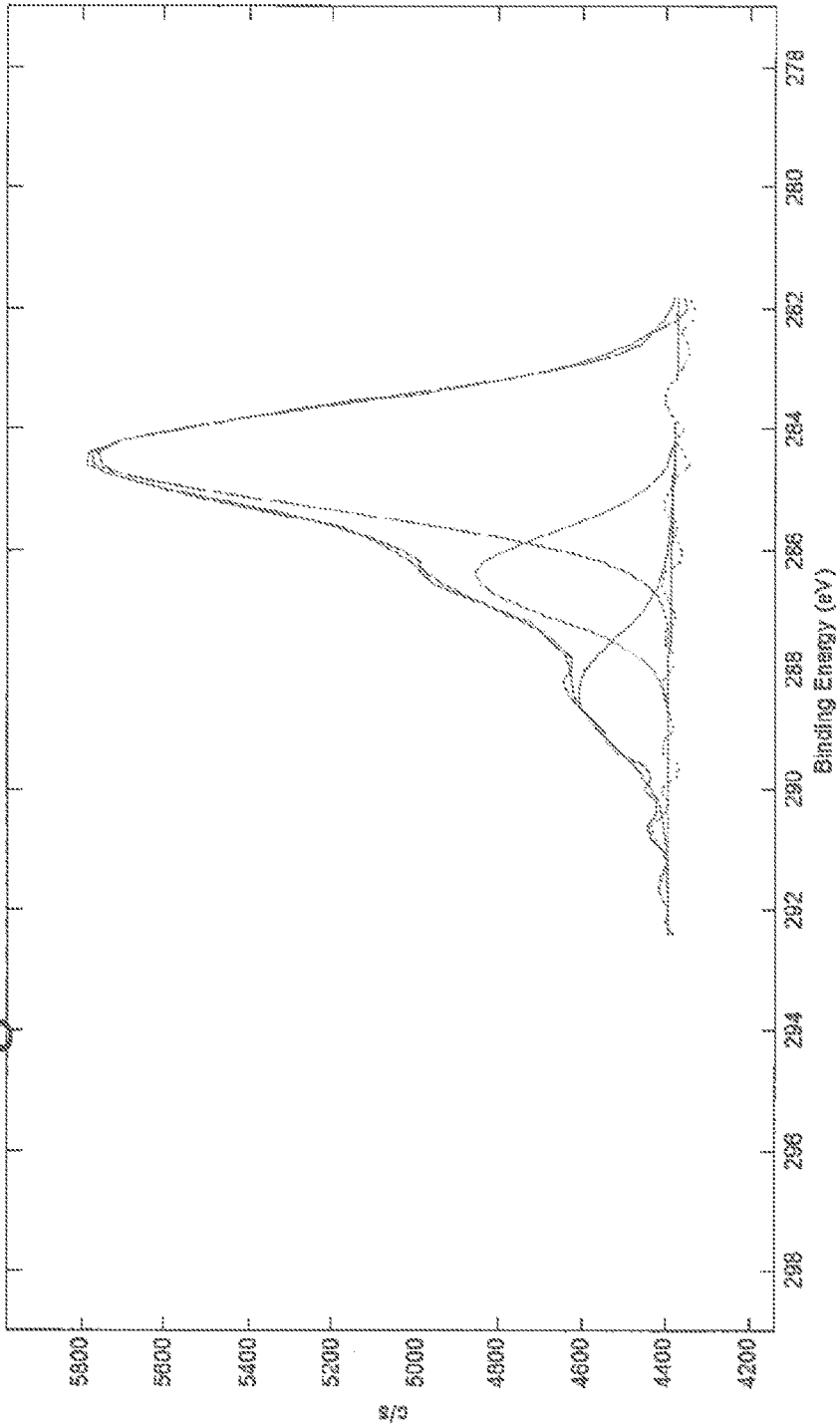
FIG. 7 provides a high-resolution XPS graph for C1s that is similar to the PHF used and hence confirms the presence of PHF on the gold nanoparticles.

FIG. 6 provides an X-ray photoelectron spectroscopy (XPS) graph showing the type of elements found in PHF-gold nanoparticle nanocomposite. Silicon (Si) is from the substrate on which PHF-gold nanoparticles were deposited for XPS analysis. FIG. 7 provides a high-resolution XPS graph for C1s that is similar to the PHF used and hence confirms the presence of PHF on the gold nanoparticles.

Figure 8:
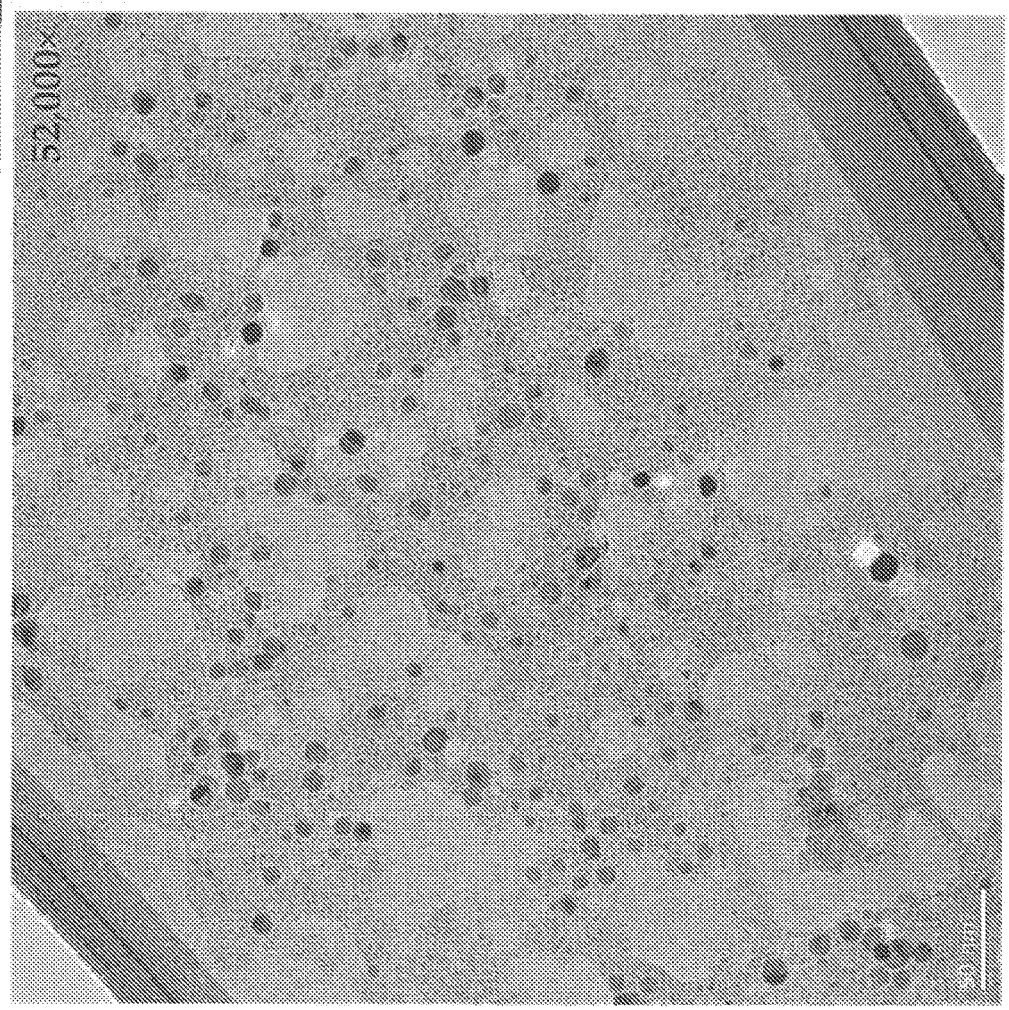
FIG. 8 provides an HR-TEM image of PHF-silver nanoparticle nanocomposites. (Magnification 52,000×)
Figure 9:
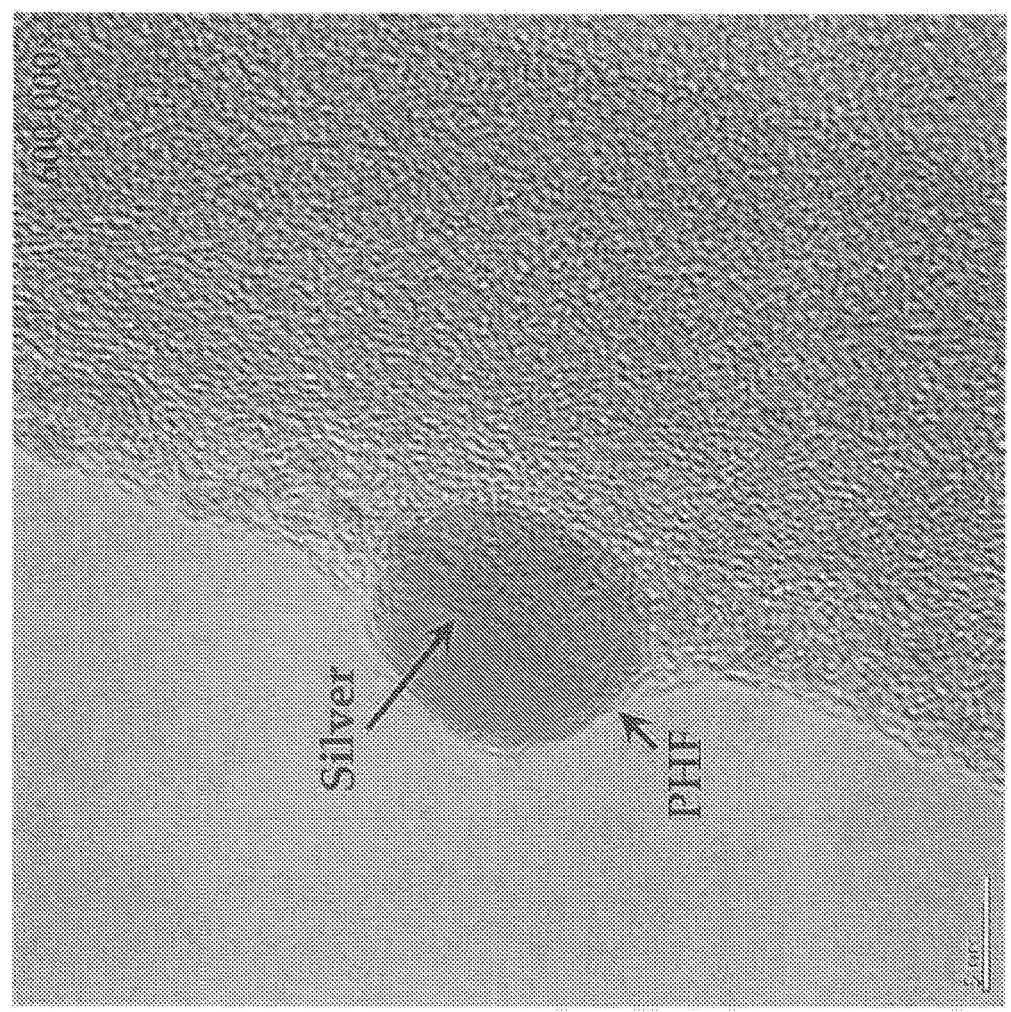
FIG. 9 provides an HR-TEM image of a single PHF-silver nanoparticle nanocomposite, showing the presence of a PHF layer surrounding a silver nanoparticle core. (Magnification 600,000×)
Figure 13:
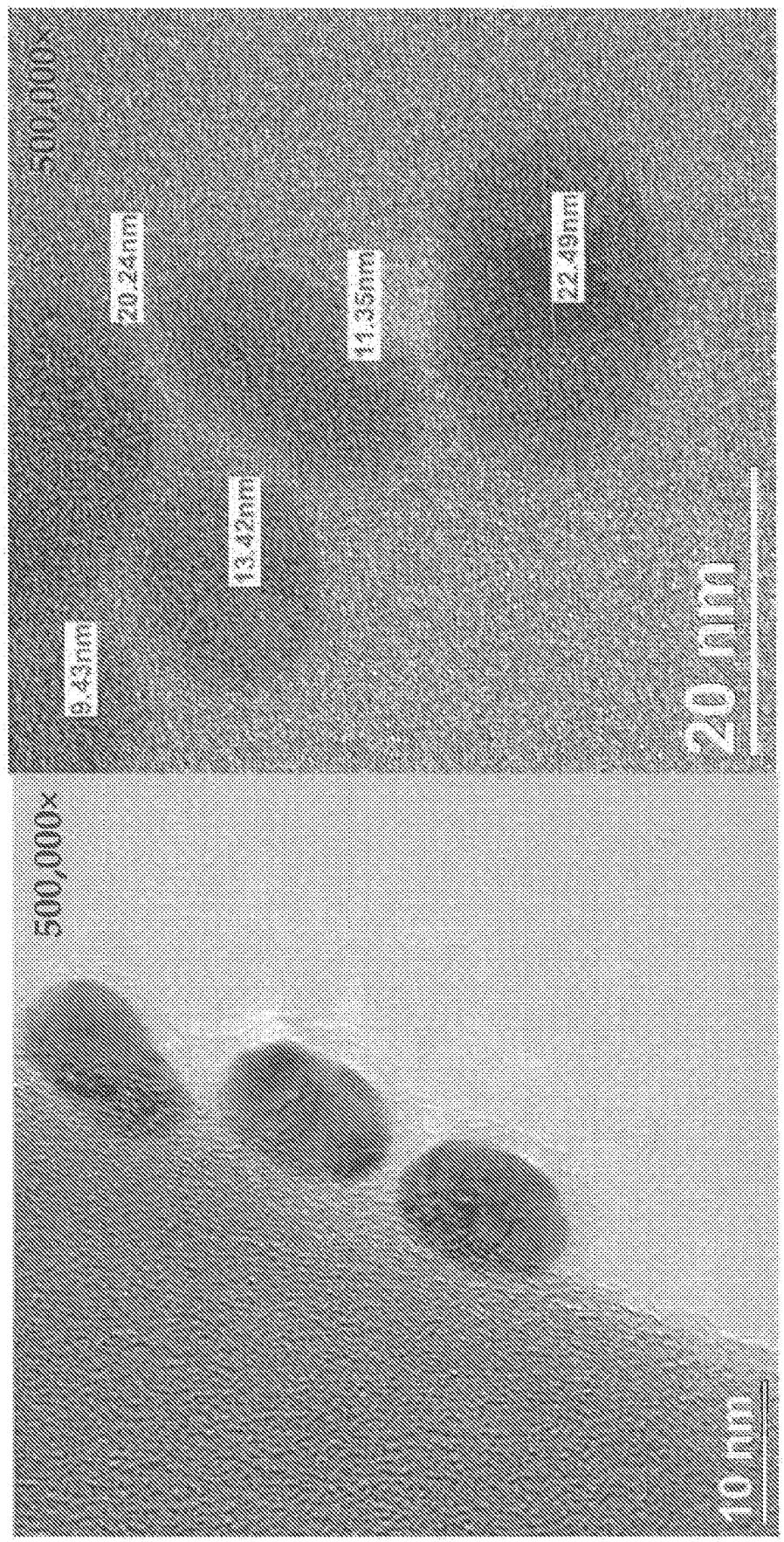
FIGS. 13A and 13B provide images showing the formation of PHF-gold nanorod nanocomposites having a length around 20 nm and width around 10 nm. (Magnification for 13A and 13B 500,000×)
Figure 14:
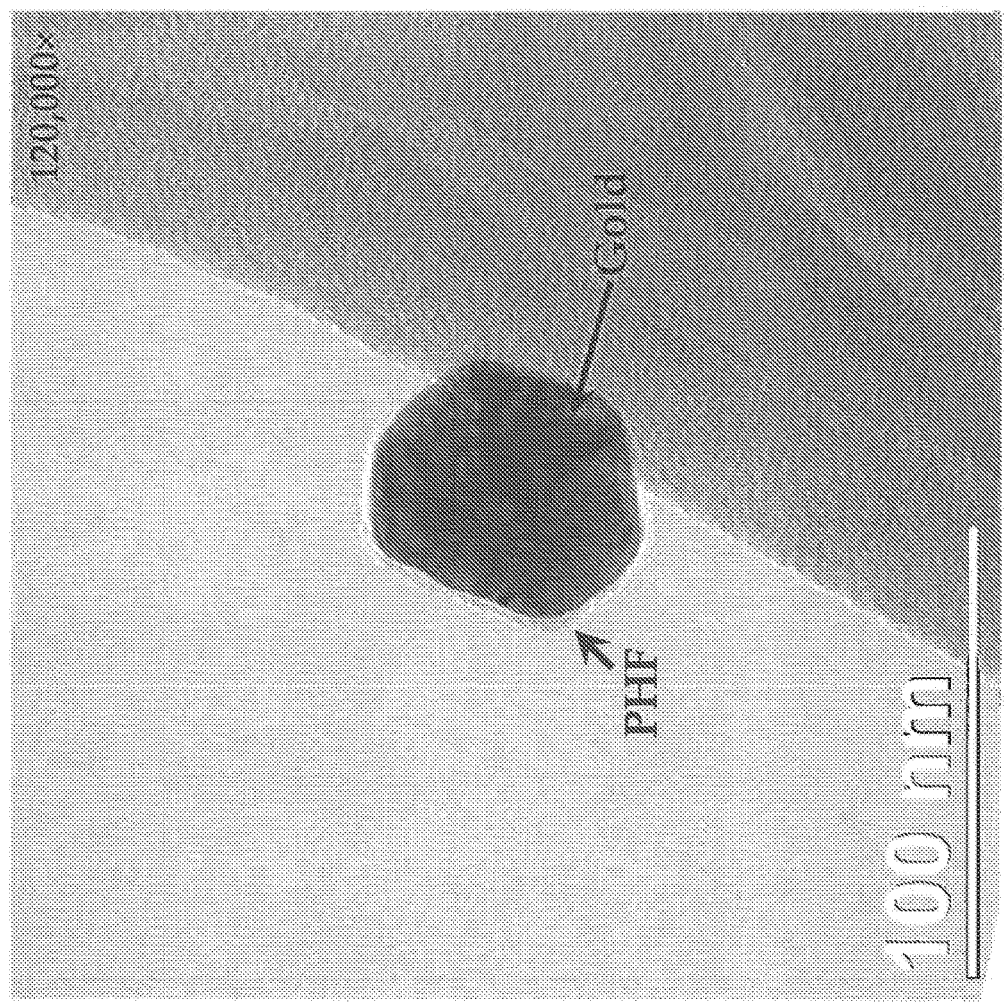
FIG. 14 provides an image showing a large PHF-gold nanoparticle nanocomposite having a size close to 80 nm. (Magnification 120,000×)
Figures 15A, 15B:
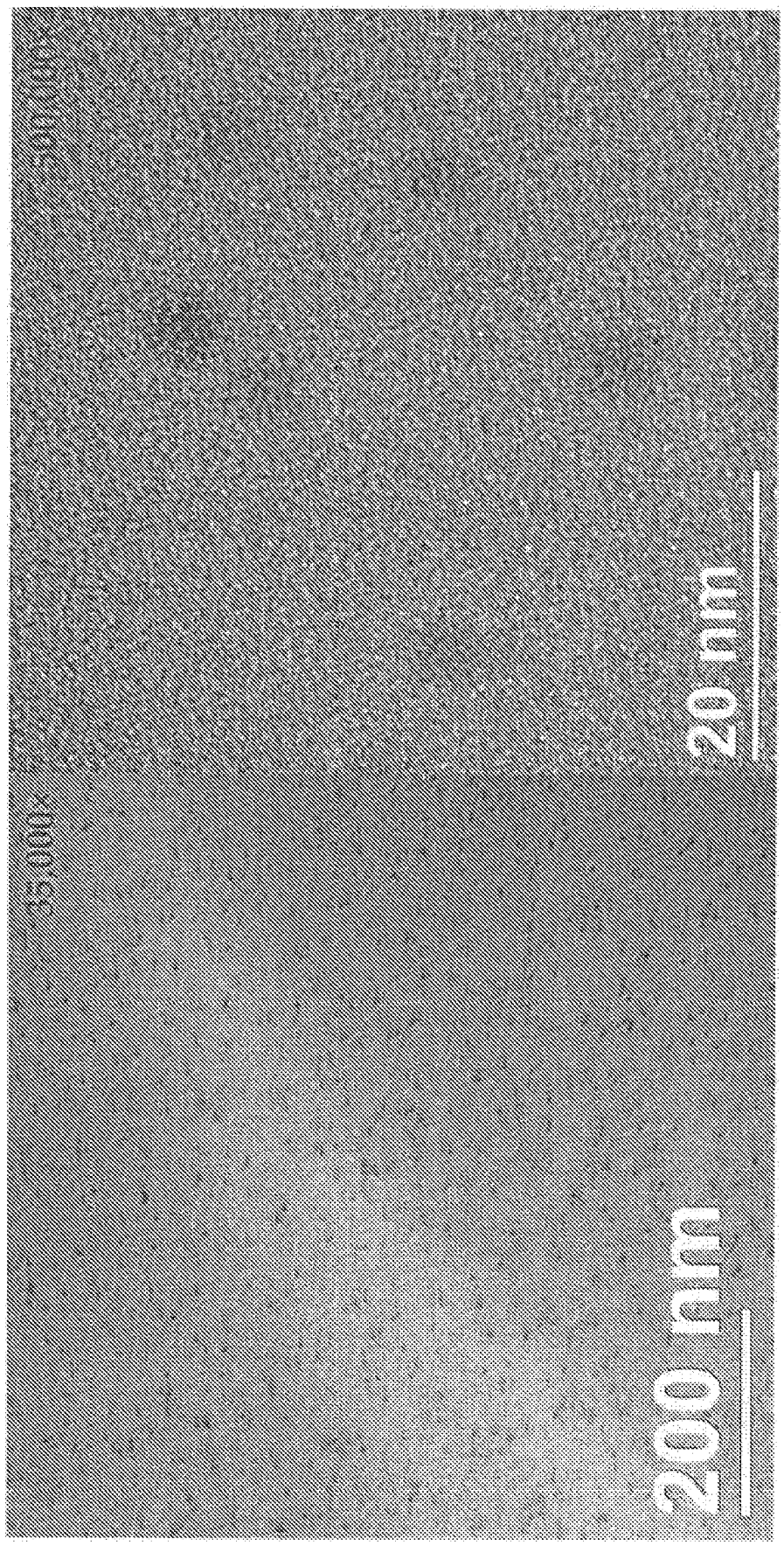
FIGS. 15A and 15B provide images showing PHF-gold nanocluster nanocomposites with uniform size distribution in the range of 3 to 5 nm. (Magnification for 15A is 35,000× and 15B is 500,000×)

FIG. 8 provides an HR-TEM image of PHF-silver nanoparticle nanocomposites at a magnification of 52,000×. FIG. 9 provides an HR-TEM image of a single PHF-silver nanoparticle nanocomposite at a magnification of 600,000×, showing the presence of a PHF layer surrounding a silver nanoparticle core. FIGS. 13A and 13B provide images at a magnification of 500,000× showing the formation of PHF-gold nanorod nanocomposites having a length around 20 nm and width around 10 nm. FIG. 14 provides an image at a magnification 120,000× showing a large PHF-gold nanoparticle nanocomposite having a size close to 80 nm. FIGS. 15A and 15B provide images showing PHF-gold nanocluster nanocomposites with uniform size distribution in the range of 3 to 5 nm. Magnification for 15A is 35,000× and 15B is 500,000×.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A fullerene-metal nanocomposite, consisting of a metal nanoparticle bonded to a functionalized fullerene compound according to the formula $C_{2n}(OH)_t(SH)_u(NH_2)_v(COOH)_w(COOM)_xO_yM_z$, wherein M is an alkali metal, alkaline earth metal, transition metal, post-transition metal, lanthanide, or actinide, n is a number ranging from 10 to 270, t is number ranging from 0 to 60, u is a number ranging from 0 to 60, v is a number ranging from 0 to 60, w is a number ranging from 0 to 60, x is a numbering ranging from 0 to 60, y is a number ranging from 0 to 30, and z is a number ranging from 0 to 30, wherein the nanocomposite is prepared by mixing a solution of metal salt or metal ion with the functionalized fullerene compound using a method in which the functionalized fullerene serves as both a reducing agent and a capping agent.

2. The fullerene-metal nanocomposite of claim 1, wherein the metal nanoparticle is selected from the group consisting of gold, silver, copper, platinum, iron, and palladium nanoparticles.

3. The fullerene-metal nanocomposite of claim 1, wherein the metal nanoparticle is a gold nanoparticle.

4. The fullerene-metal nanocomposite of claim 1, wherein u, v, w, and x are 0.

5. The fullerene-metal nanocomposite of claim 1, wherein u, v, w, x, y, and z are 0.

6. The fullerene-metal nanocomposite of claim 1, wherein n is 30.

7. The fullerene-metal nanocomposite of claim 1, wherein the metal nanoparticle has a size from 0.5 nm to 5.0 nm.

8. The fullerene-metal nanocomposite of claim 1, wherein a plurality of fullerene compounds are bonded to the outside of a metal nanoparticle core.

9. The fullerene-metal nanocomposite of claim 1, wherein a fullerene compound is within the metal nanoparticle.

10. A method of making a fullerene-metal nanocomposite, consisting essentially of the steps of:
a) mixing a solution of metal salt or metal ion with a functionalized fullerene compound according to the formula $C_{2n}(OH)_t(SH)_u(NH_2)_v(COOH)_w(COOM)_xO_yM_z$, wherein M is an alkali metal, alkaline earth metal, transition metal, post-transition metal, lanthanide, or actinide, n is a number ranging from 10 to 270, t is number ranging from 0 to 60, u is a number ranging from 0 to 60, v is a number ranging from 0 to 60, w is a number ranging from 0 to 60, x is a numbering ranging from 0 to 60, y is a number ranging from 0 to 30, and z is a number ranging from 0 to 30 in an aqueous or alcohol solution to form a fullerene-metal nanocomposite, wherein the functionalized fullerene serves as both a reducing agent and a capping agent, and b) purifying the fullerene-metal nanocomposite from the solution.

11. The method of making of claim 10, further comprising the step of adjusting the pH of the solution.

12. The method of making of claim 10, wherein the fullerene-metal nanocomposite is purified by centrifugation.

13. The method of making of claim 10, wherein the metal salt is present in solution at a concentration from 2 to 200 mg/mL.

14. The method of making of claim 10, wherein the fullerene compound is present in solution at a concentration from 1 to 20 mg/mL.

15. The method of making of claim 10, wherein the metal salt is a $HAuC_{14}$.

16. The method of making of claim 10, wherein u, v, w, x, y, and z of the fullerene compound formula are 0.

17. The method of making of claim 10, wherein n of the fullerene compound formula is 30.

18. The method of making of claim 10, wherein the solution is a water solution.

19. An antimicrobial surface, comprising:
a substrate surface; and
a coating on the substrate surface comprising a fullerene-metal nanocomposite, comprising a metal nanoparticle bonded to a functionalized fullerene compound according to the formula $C_{2n}(OH)_t(SH)_u(NH_2)_v(COOH)_w(COOM)_xO_yM_z$, wherein M is an alkali metal, alkaline earth metal, transition metal, post-transition metal, lanthanide, or actinide, n is a number ranging from 10 to 270, t is number ranging from 0 to 60, u is a number ranging from 0 to 60, v is a number ranging from 0 to 60, w is a number ranging from 0 to 60, x is a numbering ranging from 0 to 60, y is a number ranging from 0 to 30, and z is a number ranging from 0 to 30, wherein the substrate surface comprises a porous membrane, a porous filter, or surgical clothing, or the outer surface of a medical device, wherein the medical device is a pacemaker, defibrillator, neurostimulator, ophthalmic implant, an implantable shunt, an artificial joint, a hip implant, a knee implant, a catheter, a stent, an implantable coil, a pump, an intrauterine device (IUD), a heart valve, a surgical fastener, a surgical staple, a surgical pin, a surgical screw, a suture, a retractor, a bariatric balloon, an orthodontic brace, a breast implant, a surgical sponge, a gauze, a mesh pouch or a wound packing material.

20. An antimicrobial surface, comprising:
a substrate surface; and
a coating on the substrate surface comprising a polymer and a fullerene-metal nanocomposite, comprising a metal nanoparticle bonded to a functionalized fullerene compound according to the formula $C_{2n}(OH)_t(SH)_u(NH_2)_v(COOH)_w(COOM)_xO_yM_z$, wherein M is an alkali metal, alkaline earth metal, transition metal, post-transition metal, lanthanide, or actinide, n is a number ranging from 10 to 270, t is number ranging from 0 to 60, u is a number ranging from 0 to 60, v is a number ranging from 0 to 60, w is a number ranging from 0 to 60, x is a numbering ranging from 0 to 60, y is a number ranging from 0 to 30, and z is a number ranging from 0 to 30.

21. The antimicrobial surface of claim 20, wherein the metal nanoparticle is a gold nanoparticle.

22. The antimicrobial surface of claim 20, wherein u, v, w, x, y, and z of the fullerene compound formula are 0.

23. The antimicrobial surface of claim 20, wherein the substrate surface comprises the outer surface of a medical device.

24. The antimicrobial surface of claim 20, wherein the substrate surface comprises a porous membrane or porous filter.

25. The antimicrobial surface of claim 20, wherein the metal nanoparticle is a gold nanoparticle.

26. The antimicrobial surface of claim 20, wherein u, v, w, x, y, and z of the fullerene compound formula are 0.

* * * * *